United States Patent
Rainer et al.

(10) Patent No.: US 7,022,478 B2
(45) Date of Patent: Apr. 4, 2006

(54) METHODS FOR EVALUATING STROKE OR CARDIAC ISCHEMIA BY NUCLEIC ACID DETECTION

(75) Inventors: Timothy Hudson Rainer, Shatin (HK); Yuk Ming Dennis Lo, Kowloon (HK); Yuk Lan Lam, Tseng Kwan O (HK); Lawrence Ka Sing Wong, Mid Levels (HK)

(73) Assignee: The Chinese University of Hong Kong, Shatin (HK)

( * ) Notice: Subject to any disclaimer, the term of this patent is extended or adjusted under 35 U.S.C. 154(b) by 254 days.

(21) Appl. No.: 10/194,523

(22) Filed: Jul. 11, 2002

(65) Prior Publication Data

US 2003/0219759 A1 Nov. 27, 2003

Related U.S. Application Data

(60) Provisional application No. 60/380,719, filed on May 14, 2002.

(51) Int. Cl.
*C12Q 1/68* (2006.01)
*C12P 19/34* (2006.01)
*C07H 21/02* (2006.01)
*C07H 21/04* (2006.01)

(52) U.S. Cl. .................. 435/6; 435/91.2; 536/23.1; 536/24.3

(58) Field of Classification Search ................ 435/6, 435/91.2; 536/23.1, 24.3
See application file for complete search history.

(56) References Cited

U.S. PATENT DOCUMENTS 6,329,179 B1 12/2001 Kopreski

FOREIGN PATENT DOCUMENTS

| WO | WO 98/14617 A1 | 4/1998 |
| WO | WO 01/42504 A2 | 6/2001 |
| WO | WO 02/02812 A2 | 1/2002 |
| WO | WO 03/009806 A2 | 2/2003 |

OTHER PUBLICATIONS

Fournie, G. J. et al., "Plasma DNA as Cell Death Marker in Elderly Patients", Gerontology, vol. 39, pp. 215-221 (1993).*

Wijeratne, S. et al., "Cell-Free Plasma DNA as a Prognostic Marker in Intensive Treatment Unit Patients", Ann. N.Y. Acad. Sci. vol. 1022, pp. 232-238 (2004).*

Abraha, H.D. et al. "Serum S-100 protein, relationship to clinical outcome in acute stroke," *Ann. Clin. Biochem.* 1997, pp. 366-370, vol. 34.

Büttner, T. et al. "S-100 protein: serum marker of focal brain damage after ischemic territorial MCA infarction," *Stroke* 1997, pp. 1961-1965, vol. 28.

(Continued)

*Primary Examiner*—Jeffrey Fredman
*Assistant Examiner*—Teresa Strzelecka
(74) *Attorney, Agent, or Firm*—Townsend and Townsend and Crew LLP

(57) ABSTRACT

This invention relates to the use of a blood sample from a patient for evaluating stroke or cardiac ischemia in the patient.

14 Claims, 2 Drawing Sheets

OTHER PUBLICATIONS

Chen, X. Q. et al. "Microsatellite alterations in plasma DNA of small cell lung cancer patients," *Nat. Med.* 1996, pp. 1033-1035, vol. 2.

Dasi, F. et al. "Real-time quantification in plasma of human telomerase reverse transcriptase (hTERT) mRNA: a simple blood test to monitor disease in cancer patients," *Laboratory Invest.* may 2001, pp. 767-769, vol. 81, No. 5.

Lo, Y.M.D. et al. "Plasma DNA as a prognostic marker in trauma patients," *Clin. Chem.* 2000, pp. 319-323, vol. 46, No. 3.

Lo, Y.M.D. et al. "Prenatal diagnosis of fetal RhD status by molecular analysis of maternal plasma," *N. Engl. J. Med.* 1998, pp. 1734-1738, vol. 339.

Lo, Y.M.D. et al. "Presence of donor-specific DNA in plasma of kidney and liver-transplant recipients," *Lancet* 1998, pp. 1329-1330, vol. 351.

Lo, Y.M.D. et al. "Presence of fetal DNA in maternal plasma and serum," *Lancet* 1997, pp. 485-487, vol. 350.

Lo. Y.M.D. et al. "Quantitative analysis of fetal DNA in maternal plasma and serum: implications for noninvasive prenatal diagnosis," *Am. J. Hum. Genet.* 1998, pp. 768-775, vol. 62.

Nawroz, H. et al. "Microsatellite alterations in serum DNA of head and neck cancer patients," *Nat. Med.* 1996, pp. 1035-1037, vol. 2.

Nomoto, S. et al. "Mitochondrial D-loop mutations as clonal markers in multicentric hepatocellular carcinoma and plasma," *Clin. Can. Res.* Feb. 2002, pp. 481-487, vol. 8.

Stevens, H. et al. "Neurone-specific enolase and N-acetyl-aspartate as potential peripheral markers of ischaemic stroke," *Eur. J. of Clin. invest.* 1999, pp. 6-11, vol. 29.

Wunderlich, M.T. et al. "Early neurobehavioral outcome after stroke is related to release of neurobiochemical markers of brain damage," *Stroke* 1999, pp. 1190-1195, vol. 30.

Zhong, S. et al. "Presence of mitochondrial tRNALeu(UUR) A to G 3243 mutation in DNA extracted from serum and plasma of patients with type 2 diabetes mellitus," *J. Clin. Pathol.* 2000, pp. 466-469, vol. 53.

* cited by examiner

```
                        SEQUENCE LISTING

<160> NUMBER OF SEQ ID NOS: 3

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence:PCR
      amplification primer beta-globin-354F

<400> SEQUENCE: 1
gtgcacctga ctcctgagga ga                                              22

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence:PCR
      amplification primer beta-globin-455R

<400> SEQUENCE: 2
ccttgatacc aacctgccca g                                               21

<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence:dual labeled
      fluorescent PCR probe beta-globin-402T
<220> FEATURE:
<221> NAME/KEY: modified_base
<222> LOCATION: (1)
<223> OTHER INFORMATION: n = a modified by VIC
<220> FEATURE:
<221> NAME/KEY: modified_base
<222> LOCATION: (26)
<223> OTHER INFORMATION: n = g modified by TAMRA and 3' blocking
      phosphate group
```

```
<400> SEQUENCE: 3
naggtgaacg tggatgaagt tggtgn                                          26
```

METHODS FOR EVALUATING STROKE OR CARDIAC ISCHEMIA BY NUCLEIC ACID DETECTION

CROSS REFERENCE TO RELATED APPLICATIONS

The present application claims priority to U.S. Ser. No. 60/380,719 filed May 14, 2002 herein incorporated by reference in its entirety.

FIELD OF THE INVENTION

This invention relates to the detection of nucleic acids in the blood plasma or serum of a patient for evaluating stroke or cardiac ischemia in the patient.

BACKGROUND OF THE INVENTION

Stroke and heart disease rank as leading causes of deaths worldwide accounting for many millions of victims per year. Preventive strategies have resulted in a decrease in the rate of stroke, heart attack, and death but these improvements have been offset in part by the growth of an aging population. Methods of simply and accurately evaluating these disease conditions in patients are needed in order to aid in the detection, diagnosis, prognosis, monitoring or treatment of these conditions worldwide.

Recently, interest has developed in the use of circulating nucleic acids in the plasma or serum of patients for clinical diagnosis. (See, Lo Y M D et al., *N. Engl. J. Med.* 1998; 339:1734–8; Lo Y M D, et al., *Lancet* 1997; 350:485–7; Lo Y M D, et al., *Am. J. Hum. Genet.* 1998; 62:768–75; Chen X Q, et al., *Nat. Med.* 1996; 2:1033–5, Nawroz H et al., *Nat. Med.* 1996; 2:1035–7; Lo Y M D et al., *Lancet* 1998; 351:1329–30; Lo Y M D, et al., *Clin. Chem.* 2000; 46:319–23.) Although the mechanisms by which nucleic acids are released into the circulation are unknown, it is likely that cell death is one major factor (Fournie et al., *Gerontology* 1993; 39:215–21; Fournie et al., *Cancer Lett.* 1995; 91:221–7.) In this application, for the first time, it is demonstrated that the detection of circulating nucleic acids in the plasma or serum of stroke or cardiac ischemia patients can be used for the evaluation of disease in the patient.

BRIEF SUMMARY OF THE INVENTION

The present invention provides methods of evaluating the disease condition of a stroke patient. In one embodiment the method includes obtaining a sample of blood plasma or serum from a stroke patient, detecting the quantity of nucleic acid in the sample, and evaluating the disease condition by comparing the quantity of nucleic acid in the sample to a control.

In one aspect of the present invention, the stroke is hemorrhagic.

In a second aspect of the present invention, the stroke is ischemic.

In a third aspect of the present invention, the nucleic acid in the sample is DNA. In one embodiment, the DNA is selected from the group consisting of DNA sequences from the beta-globin, RHD, and albumin genes. In a second embodiment, the DNA detected is DNA sequences of the beta globin gene.

In a fourth aspect of the present invention, the nucleic acid in the sample is RNA.

In a fifth aspect of the present invention, the detection step further comprises contacting the sample with a polynucleotide that selectively hybridizes to the beta-globin gene.

In a sixth aspect, the present invention further comprises the step of amplifying the nucleic acid. In one embodiment, the nucleic acid is DNA and the DNA is amplified using PCR. In a second embodiment, the nucleic acid is RNA and the RNA is amplified using reverse-transcriptase PCR.

In a seventh aspect of the present invention, the nucleic acid is DNA and the DNA is amplified using real-time PCR.

In an eighth aspect, the nucleic acid is RNA and the RNA is amplified using reverse transcriptase real-time PCR.

In a ninth aspect, the nucleic acid is DNA and the DNA is amplified using the primers disclosed in SEQ ID NO:1 and SEQ ID NO:2.

In a tenth aspect of the present invention, the quantity or concentration of nucleic acid in the sample is different than in the control. In one embodiment, the quantity or concentration of nucleic acid in the sample is higher than in the control.

In an eleventh aspect of the present invention, the sample is obtained within 24 hours of onset of stroke-like symptoms in the patient.

In a twelfth aspect, the sample is obtained within 3 hours of onset of stroke-like symptoms in the patient.

In a thirteenth aspect of the present invention, the present invention provides methods of evaluating the disease condition of a cardiac ischemia patient. In one embodiment, the method includes obtaining a sample of blood plasma or serum from a cardiac ischemia patient, detecting the quantity or concentration of nucleic acid in the sample, and evaluating the disease condition by comparing the quantity or concentration of nucleic acid in the sample to a control.

In a fourteenth aspect of the present invention, the cardiac ischemia is selected from the group consisting of acute myocardial infarction, asymptomatic coronary artery disease, stable angina, unstable angina, and acute myocardial infarction.

In a fifteenth aspect of the present invention, the nucleic acid in the sample is DNA.

In a sixteenth aspect, the nucleic acid in the sample is RNA.

In a seventeenth aspect of the present invention, the invention further comprises the step of amplifying the nucleic acid. In one embodiment, the nucleic acid amplified is DNA. In a second embodiment, the nucleic acid is DNA and the DNA is amplified using PCR. In a third embodiment, the DNA is amplified using real-time PCR. In a fourth embodiment, the nucleic acid is RNA and the RNA is amplified using reverse transcriptase PCR. In a fifth embodiment, the RNA is amplified using reverse transcriptase real-time PCR.

In an eighteenth aspect of the present invention, the quantity or concentration of nucleic acid in the sample is different than in the control. In one embodiment, the quantity or concentration of nucleic acid in the sample is higher than in the control.

In a nineteenth aspect of the present invention, the sample is obtained within 24 hours of onset of ischemia in the patient.

In a twentieth aspect, the sample is obtained within 3 hours of onset of ischemia in the patient.

Definitions

The phrase "evaluating a disease condition" refers to assessing the disease condition of a patient. For example, evaluating the condition of a patient can include detecting the presence or absence of the disease in the patient. Once the presence of disease in the patient is detected, evaluating the disease condition of the patient may include determining the severity of disease in the patient. It may further include using that determination to make a disease prognosis, e.g. a life-span prediction or treatment plan. Evaluating the condition of a patient may also include detecting that a patient no longer has a disease condition but has suffered from the disease condition in the past. For example, the patient might have had a stroke or acute myocardial infarction in the past but the patient may no longer be suffering from the stroke or acute myocardial infarction. Evaluating the disease condition in that instant might also include determining the probability of reoccurrence of the disease condition or monitoring the reoccurrence in a patient. For example, detecting two strokes or acute ischemic cardiac events occurring within minutes, hours, or days of each other. Evaluating the disease condition might also include monitoring a patient for signs of disease. Evaluating a disease condition therefore includes detecting, diagnosing, or monitoring a disease condition in a patient as well as determining a patient prognosis or treatment plan. The method of evaluating a disease condition aids in risk stratification A "stroke" patient is an individual who is currently suffering from a stroke or stroke-like symptoms, who has in the past suffered from a stroke or stroke-like symptoms or who is at risk for developing a stroke. A stroke may be hemorrhagic or ischemic. An ischemic "stroke" refers to the loss or alteration of bodily function that results from an insufficient supply of blood to the brain. The insufficient supply of blood may be as a result of an obstruction of blood flow to the brain. The severity of a stroke may depend on the size of the obstruction or the length of time that the blood flow is obstructed. For example, if blood is obstructed for more than several minutes, the damage to the brain cells becomes permanent and tissue dies in the affected region. In contrast, a hemorrhagic stroke refers to a stroke which results from the rupture of vascular lesions and the release of blood into the surrounding brain tissue. Stroke-like symptoms might include facial droops, arm drift or weakness, abnormal speech, hyperglycemia, hypoglycemia, unilateral numbness, visual disturbances or dizziness. Further clinical manifestations and diagnostic parameters of "stroke" are described in detail in Harrison's Principles of Internal Medicine, 14$^{th}$ Edition, Volume 2. Non hemorrhagic strokes may also be classified according to definitions used in the TOAST trial, (See Adams et al. *Stroke* 1993; 24:35–41).

Blood plasma refers to the fraction of whole blood resulting from low speed centrifugation of blood treated with anticoagulants. Blood serum refers to the watery portion of fluid remaining after a blood sample has coagulated.

A "cardiac ischemia" patient refers to an individual who is currently suffering from cardiac ischemia, who has in the past suffered from cardiac ischemia or who is at risk for developing cardiac ischemia. The term "cardiac ischemia" refers to a condition characterized by a reduced blood flow to the heart leading to a lack of oxygen delivery to cardiac tissue cells. For example, acute coronary syndrome which includes coronary artery disease and varying degrees of cardiac ischemia involves a spectrum of pathological and clinical presentations including asymptomatic coronary artery disease, stable angina, unstable angina or acute myocardial infarction. Further clinical manifestations and diagnostic parameters of "cardiac ischemia" are described in detail in Harrison's Principles of Internal Medicine, 14$^{th}$ th Edition, Volume 2.

The phrase "comparing the quantity of nucleic acid in the sample to a control" refers to measuring the amount or concentration of nucleic acid in a sample obtained from one patient and comparing it to the amount or concentration of nucleic acid in a second sample. For example, the amount or concentration of nucleic acid in the first sample may be compared to the amount or concentration of nucleic acid in a second sample taken from the same individual at an earlier time. In another example, the second sample may be a sample obtained from a second individual. The second individual may be healthy or diseased. The second individual may have suffered from cardiac ischemia or stroke. In other embodiments, the control might not be a second sample but instead an average of data from a variety of persons who are classified as healthy or suffering from various stroke conditions or cardiac ischemic conditions. The data collected may indicate various levels or concentration of nucleic acid in the blood and correspond those levels to severity, prognosis or diagnosis of disease. For example, using the methods of the present invention, a skilled practitioner can compare the amount or concentration of nucleic acid in the sample to the control and determine the presence or absence of disease in the individual from whom which the sample was obtained. The skilled practitioner can also use the comparison to determine stroke type, e.g., ischemic or hemorrhagic, or stage of coronary disease, e.g., stable angina, unstable angina, acute myocardial infarction. The skilled practitioner might also use the comparison to determine disease severity or predict patient life-span. The skilled practitioner can use the comparison to aid in risk stratification, monitoring or treatment of the disease condition in a patient. In some embodiments, total amount of nucleic acid is detected.

"Nucleic acid" refers to a deoxyribonucleotide or ribonucleotide polymer in either single- or double-stranded form, and unless otherwise limited, would encompass known analogs of natural nucleotides that can function in a similar manner as naturally occurring nucleotides.

The phrase "a sample of blood plasma or serum", as used herein, refers to a sample blood plasma or serum obtained from a subject. Frequently the sample will be a "clinical sample" which is a sample derived from a patient with a disease or suspected of having a disease (a "patient"). The sample as initially obtained from the patient may contain additional components other than blood plasma or serum. For example, the sample may initially be a sample of whole blood purified to its plasma or serum components. Either "fresh" blood plasma or serum, or frozen (stored) and subsequently thawed plasma or serum may be used for the methods of this invention. Frozen (stored) plasma or serum should optimally be maintained at storage conditions of –20 to –70 degrees centigrade until thawed and used.

The terms "hybridize(s) specifically" or "specifically hybridize(s)" refer to complementary hybridization between an oligonucleotide (e.g. a primer or labeled probe) and a target sequence. The term specifically embraces minor mismatches that can be accommodated by reducing the stringency of the hybridization conditions to achieve the desired priming for the PCR polymerases or detection of hybridization signal.

The term "oligonucleotide" refers to a molecule comprised of two or more deoxyribonucleotides or ribonucleotides, such as primers, probes, and other nucleic acid fragments. The exact size of an oligonucleotide depends on many factors and the ultimate function or use of the oligonucleotide. "Adding" an oligonucleotide refers to joining an oligonucleotide to another nucleic acid molecule. Typically, adding the oligonucleotide is performed by ligating the oligonucleotide using a DNA ligase.

The term "primer" refers to an oligonucleotide, whether natural or synthetic, capable of acting as a point of initiation of DNA synthesis under conditions in which synthesis of a primer extension product complementary to a nucleic acid strand is induced, i.e., in the presence of four different nucleoside triphosphates and an agent for polymerization (such as DNA polymerase or reverse transcriptase) in an appropriate buffer and at a suitable temperature. A primer is preferably a single-stranded oligodeoxyribonucleotide sequence. The appropriate length of a primer depends on the intended use of the primer but typically ranges from about 15 to about 30 nucleotides. Short primer molecules generally require cooler temperatures to form sufficiently stable hybrid complexes with the template. A primer need not reflect the exact sequence of the template but must be sufficiently complementary to specifically hybridize with a template.

"Probe" refers to an oligonucleotide which binds through complementary base pairing to a subsequence of a target nucleic acid. It will be understood by those skilled in the art that probes will typically substantially bind target sequences lacking complete complementarity with the probe sequence depending upon the stringency of the hybridization conditions. The probes are typically directly labeled (e.g., with isotopes or fluorescent moieties) or indirectly labeled such as with digoxigenin or biotin. By assaying for the presence or absence of the probe, one can detect the presence or absence of the target.

The nucleic acids may be single stranded or double stranded, as specified, or contain portions of both double stranded or single stranded sequence. The depiction of a single strand also defines the sequence of the complementary strand; thus the sequences described herein also provide the complement of the sequence. The nucleic acid may be DNA, both genomic and cDNA, RNA or a hybrid, where the nucleic acid may contain combinations of deoxyribo- and ribo-nucleotides, and combinations of bases, including uracil, adenine, thymine, cytosine, guanine, inosine, xanthine, hypoxanthine, isocytosine, isoguanine, etc. "Transcript" typically refers to a naturally occurring RNA, e.g., a pre-mRNA, hnRNA, or mRNA. As used herein, the term "nucleoside" includes nucleotides and nucleoside and nucleotide analogs, and modified nucleosides such as amino modified nucleosides. In addition, "nucleoside" includes non-naturally occurring analog structures. Thus, e.g. the individual units of a peptide nucleic acid, each containing a base, are referred to herein as a nucleoside.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The term "substantially identical" indicates that two or more nucleotide sequences share a majority of their sequences. Generally, this will be at least about 90% of their sequences and preferably about 95% of their sequences. Another indication that the sequences are substantially identical is if they hybridize to the same nucleotide sequence under stringent conditions (see, e.g., Sambrook and Russell, eds, *Molecular Cloning: A Laboratory Manual*, 3rd Ed, vols. 1–3, Cold Spring Harbor Laboratory Press, 2001; and *Current Protocols in Molecular Biology*, Ausubel, ed. John Wiley & Sons, Inc. New York, 1997). Stringent conditions are sequence-dependent and will be different in different circumstances. Generally, stringent conditions are selected to be about 5° C. (or less) lower than the thermal melting point ($T_m$) for the specific sequence at a defined ionic strength and pH. The $T_m$ of a DNA duplex is defined as the temperature at which 50% of the nucleotides are paired and corresponds to the midpoint of the spectroscopic hyperchromic absorbance shift during DNA melting. The $T_m$ indicates the transition from double helical to random coil Typically, 'stringent conditions' will be those in which the salt concentration is about 0.2×SSC at pH 7 and the temperature is at least about 60° C. For example, a nucleic acid of the invention or fragment thereof can be identified in standard filter hybridizations using the nucleic acids disclosed here under stringent conditions, which for purposes of this disclosure, include at least one wash (usually two) in 0.2×SSC at a temperature of at least about 60° C., usually about 65° C., sometimes 70° C. for 20 minutes, or equivalent conditions. For polymerase chain reaction (PCR), an annealing temperature of about 5° C. below $T_m$, is typical for low stringency amplification, although annealing temperatures may vary between about 32° C. and 72° C., e.g., 40° C., 42° C., 45° C., 52° C., 55° C., 57° C., or 62° C., depending on primer length and nucleotide composition. or high stringency PCR amplification, a temperature at, or slightly (up to 5° C.) above, primer $T_m$ is typical, although high stringency annealing temperatures can range from about 50° C. to about 72° C., and are often 72° C., depending on the primer and buffer conditions (Ahsen et al., *Clin. Chem.* 47:1956–61, 2001). Typical cycle conditions for both high and low stringency amplifications include a denaturation phase of 90° C.–95° C. for 30 sec.–2 min., an annealing phase lasting 30 sec.–2 min. and an extension phase of about 72° C. for 1–6 min.

The terms "identical" or "percent identity", in the context of two or more nucleic acids, refer to two or more sequences or subsequences that are the same or have a specified percentage of nucleotides that are the same (i.e., about 70% identity, preferably 75%, 80%, 85%, 90%, or 95% identity over a specified region, when compared and aligned for maximum correspondence over a comparison window, or designated region as measured using BLAST or BLAST 2.0 sequence comparison algorithms with default parameters described below, or by manual alignment and visual inspection. Such sequences are then said to be "substantially identical." This definition also refers to the complement of a test sequence. Preferably, the identity exists over a region that is at least about 15, 20 or 25 nucleotides in length, or more preferably over a region that is 50–100 nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 15 to 600, (usually about 20 to about 200, or more usually about 50 to about 150) in which a sequence may be compared to a reference sequence of the same number of contiguous positions after the two sequences are optimally aligned.

Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389–3402 (1977) and Altschul et al., *J. Mol. Biol.* 215:403–410 (1990), respectively. BLAST and BLAST 2.0 are used, with the default parameters described herein, to determine percent sequence identity for the nucleic acids described herein. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, M=5, N=–4 and a comparison of both strands.

The BLAST algorithm also performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

DETAILED DESCRIPTION OF THE INVENTION

Figure 1:
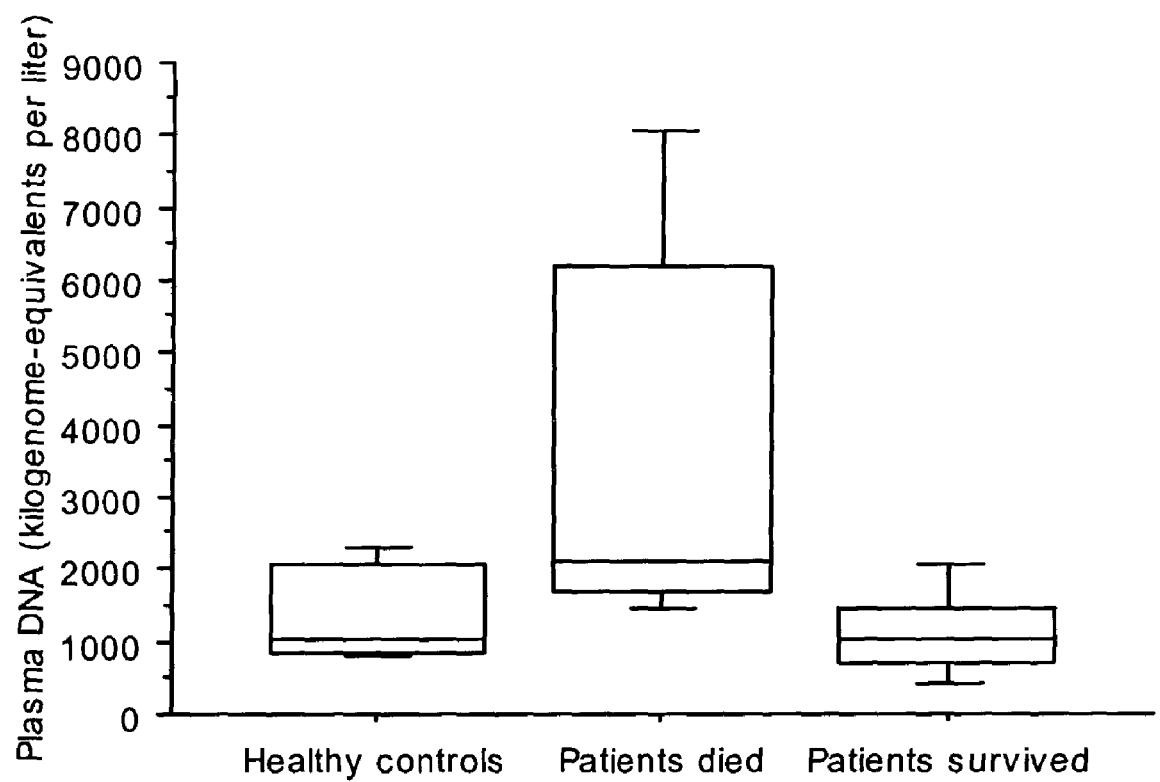
FIG. 1. Plasma DNA concentrations in control patients and in stroke patients who survived to discharge or died within 28 days of symptom onset. Plasma DNA concentrations as determined by real-time quantitative PCR for the β-globin gene (y-axis) are plotted against patient categories (x-axis). The lines inside the boxes denote medians whilst the boxes mark the interval between the $25^{th}$ and $75^{th}$ percentiles. The whiskers denote the interval between the $10^{th}$ and $90^{th}$ percentiles. The difference between the groups is statistically significant (P=0.005; Kruskal-Wallis test).

This invention pertains to the surprising discovery that circulating levels of nucleic acid, e.g., RNA or DNA, can be found in the blood plasma or serum of stroke or cardiac ischemia patients. The methods of the present invention provide for the detection and quantification of nucleic acids in a patient for the evaluation of a disease condition in the patient.

It is particularly surprising that circulating nucleic acids in the blood plasma or serum of a stroke patient can be detected. It has long been recognized that the central nervous system (CNS) is a privileged compartment within an animal, and that transport between the blood and the CNS is less rapid, more difficult and more closely regulated than transport between the blood and other body compartments. The "blood-brain barrier" ("BBB") is the term used to describe this functional barrier between the CNS and the blood of an animal. It is therefore unexpected that nucleic acid markers for stroke, a disease of the CNS, can pass through the BBB and be detected in the blood plasma or serum of a patient. Detection and quantification of nucleic acid markers in the plasma or serum of a stroke patient is an effective way to evaluate the stroke disease condition in the patient.

The detection and quantification of nucleic acid markers in the plasma or serum of a cardiac ischemia patient also presents a very effective way to evaluate a cardiac ischemic disease condition in a patient. For example, the methods of the present invention are more effective than conventional methods to evaluate cardiac ischemia in instances where a patient suffers from more than one ischemic event in a short time period because of the increased kinetics associated with plasma nucleic acid and its short half-life in the circulatory system (See Lo Y M D et al. *Am J Hum Genet* 1999; 64:218–224).

The present invention therefore describes a method by which nucleic acid, e.g., DNA or RNA, in plasma or serum can be detected and thus used for the evaluation, e.g., diagnosis, prognosis, treatment, or monitoring of stroke conditions or cardiac ischemic conditions, e.g., stable angina, unstable angina, acute myocardial infarction, in a patient. The method utilizes nucleic acid amplification assays to detect nucleic acid, both particle associated nucleic acid and nonparticle associated nucleic acid circulating in the plasma or serum of individuals. As such, the present invention describes a novel and nonobvious way of evaluating stroke and/or cardiac ischemia in a patient.

Selecting a Patient Population

The present invention provides methods for evaluating a disease condition in stroke or cardiac ischemia patients. A stroke patient is any individual suffering from the acute occurrence of focal neurological signs lasting for more than 24 hours in a different neuroanatomical location from that of any previous stroke. A stroke patient may also be an individual suffering from the worsening of an existing stroke condition that lasted for than one week, or more than 24 hours if accompanied by a brain lesion, or an individual who has suffered from these conditions in the past or is at risk for developing them in the future. A person at risk for developing a stroke condition includes but is not limited to patients with previous transient ischemic attacks, patients with atherosclerosis, patients with atrial fibrillation, patients with heart valve disorders, patients on antiplatelet and antithrombin medication, or smokers. A skilled medical practitioner will know how to diagnose these conditions in a patient. For example, any patient diagnosed as having cerebral infarcts, cerebral hemorrhage or transient cerebral ischemic attacks is a stroke patient as well as any patient suffering from stroke-like syndromes but not known to have had a stroke.

Patients presenting with a possible stroke require a detailed and extensive clinical, laboratory and neuroimaging workup in order firstly to confirm the diagnosis, secondly to assess the severity of the stroke, thirdly to determine whether a patient should receive any specific therapy (for example, antithrombolytic medication) and fourthly to assess the likely short and long term recovery.

The diagnosis of stroke is made sometimes by exclusion and at other times by positive inclusion. Some patients present as 'stroke mimics' appearing to have a stroke but subsequent detailed clinical and laboratory assessments and investigations reveal that other conditions (for example, hypoglycemia) are the real causes rather than an acute cerebrovascular event. Thus, one of the first steps in making the diagnosis of stroke is to exclude other conditions.

A diagnosis of stroke may be confirmed by cerebral neuroimaging where this is available which includes cerebral computed axial tomography without contrast enhancement and/or magnetic resonance imaging including a diffusion-weighted MRI study (See Gilman, *N. Eng.l J. Med.* 1998; 338:889–96; Davis K R et al, *Comput. Tomogr.* 1977; 1:71–86; Linfante et al., *Stroke* 1999; 30:2263–7; Schellinger P D et al., *Stroke* 1999; 30:765–8; Tong D C et al., *Neurology* 1998; 50:864–70). Such imaging may confirm the diagnosis, help characterize the underlying pathology of hemorrhage or ischemia, direct therapeutic management and also aid prognostic evaluation and risk stratification.

Other steps in diagnosis and risk stratification may include clinical assessments using validated clinical scoring methods. Two examples are The National Institutes of Health Stroke Scale and the Glasgow Coma Score both of which may be used to some degree by skilled, trained practitioners in diagnosis, to determine severity and to predict future outcome in patients suffering from a stroke.

In patients with an acute cardiovascular event such as a stroke or cardiac ischemia, it is important to determine the effect of the acute event upon subsequent morbidity and patient disability. However, in order to determine the effect of the acute event, it is necessary to qualify or quantify the patient's ability or disability prior to the event and set baseline values against which later disability may be determined. One method of evaluating the ability or disability of a stroke patient at any point in time is to use the "Modified Rankin Scale", a simplified overall assessment of function in which a score of 0 indicates the absence of any disabling symptoms, a score of 1 indicates the ability to carry out all the usual duties and activities of a normal person despite some symptoms, a score of 2 indicates some inability to carry out all previous activities although the patient is able to look after his/her own affairs without assistance, a score of 3 indicates moderate disability with need for help to carry out some activities but able to walk without assistance, a score of 4 indicates inability to walk or attend to bodily needs without some assistance, and a score of 5 indicates severe disability characterizing a patient who is bedridden, incontinent and requiring constant nursing care and attention (Van Sweiten J C, Koudstaal P J et al., *Stroke* 1988; 19:604–7). When the assessment is made or ability prior to the acute event then it is described as the "Pre-Stroke Modified Rankin Score" whereas when the assessment is made at some time after the stroke then it is described as the "Post-Stroke Modified Rankin Score" and a time limit is included as in, for example, the six-month Post-Stroke Modified Rankin Score.

Patients with cardiac ischemia or acute coronary syndrome present in a variety of ways and may have a spectrum of underlying pathology. The diagnosis is made based on a clinical, electrocardiographic and laboratory workup which usually involves repeated or serial assessments. Clinically, the diagnosis is suggested based on symptoms such as chest pain, palpitations, dizziness, and risk factors such as smoking, diabetes mellitus, previous diagnosis of angina or myocardial infarction and family history of cardiovascular events. Characteristic changes on electrocardiograph (ECG) include ST elevation, Q and T wave abnormalities, whilst characteristic elevation of protein markers in the serum, including creatine kinase, myoglobin, lactate dehydrogenase, troponin I and troponin T. In general, the diagnosis of myocardial infarction is made based on typical abnormalities in two or more of the three workup arenas—clinical, laboratory and electrocardiography—but because acute coronary syndromes comprise a spectrum of disease, some leniency may be allowed in selecting patient populations.

Assessment of cardiac disability and prognostic evaluation is made partly by considering clinical abnormalities such as inability to walk up stairs, partly by electrocardiographic and laboratory abnormalities, also by assessing cardiac motion abnormalities by echocardiography (cardiac ultrasonography), and by cardiac angiography which may be used to demonstrate narrowing of one or more coronary arteries.

Obtaining Blood Samples

Blood sample are obtained from the patients described in the present invention. Blood can be drawn by standard methods into a collection tube, e.g., siliconized glass tube, either without anticoagulation for the preparation of serum, or with anticoagulants, e.g., EDTA, sodium citrate, or heparin. In a preferred embodiment, fractionation of plasma or serum from whole blood is performed prior to freezing. Fractionation of fresh plasma can be performed by standard methods, for example, fresh plasma or serum may be fractionated from whole blood by centrifugation according to known methods. In a preferred embodiment, centrifugation is gentle so that it does not fraction out apoptotic bodies from the plasma or serum. For some embodiments of the present invention, e.g., amplification of RNA with RT-PCR, it is preferable to pretreat heparinized blood with heparinase followed by the removal of calcium.

Isolation of Blood Plasma or Serum

Nucleic acid can be extracted from blood plasma or serum using standard extraction methods known in the art, e.g., gelatin extraction, silica, glass bead or diatom extraction, guanidine or guanidinium-based extraction, chemical extraction methods, or size exclusion or anion exchange chromatographic methods (See U.S. Pat. No. 6,329,179 and International Publication Number WO 01/42504). Nucleic acid, e.g., DNA, can also be extracted using a QIAamp Blood Kit according to the "blood and body fluid protocol" as recommended by the manufacturer (Chen X Q, et al. *Nat. Med.* 1996;2:1033–5).

In one method, nucleic acid is precipitated from plasma or serum with gelatin by a method modified from that of Fournie et al. (1986 *Anal. Biochem.* 158 250–256). A gelatin solution is prepared by mixing gelatin with water, autoclaving the mixture and filtering it through a 0.2 micron filter. The resultant solution is sequentially frozen in a dry ice/ethanol bath and thawed at room temperature. A 0.3% gelatin solution is prepared using the resultant solution. Blood plasma or serum is mixed with EDTA, sterile water, and emulsified. After centrifugation, the aqueous layer is removed and transferred to a clean tube. DNA is precipitated by adding the 0.3% gelatin solution and ethanol, followed by incubation at −20° C.

In another method, nucleic acid is extracted in an enriching method, or extracted nucleic acid is further enriched, using probe specific hybridization wherein said hybridizing probes are immobilized to a substrate, e.g., nylon or magnetic beads, from which contaminating species, e.g., unwanted nucleic acid, can be removed using known methods, e.g., stringent washings. Other extraction methods include using a magnetic or electric field.

In yet another method, nucleic acid can be extracted from blood serum or plasma by heating the serum or plasma, at a temperature from about 90° C. to about 100° C. for up to about 20 minutes.

Circulating nucleic acids can be extracted form plasma or serum using glass beads, silica particles or diatom as in the methods or adapted methods of Boom et al. (Boom et al., 1991, *J. Clin. Microbiol.* 29:1804–1811; Boom et al. 1989, *J. Clin. Microbiol.* 28:495–503). Blood plasma or serum is mixed with a silica suspension made by known methods. The mixture is then centrifuged and the supernatant is aspirated and discarded. After washing the silica-DNA pellets with washing buffer, ethanol and acetone, it is dried and then the sample is eluted with a TE buffer with or without Proteinase K. Following elution, the sample is centrifuged and the DNA-containing supernatant recovered. The skilled practitioner will know how to extract DNA or RNA from blood plasma or serum using other known methods. Any means of purifying DNA or RNA from blood plasma or serum can be used in the methods of the present invention.

Nucleic Acid Detection Methods

The nucleic acids detected in the methods of the invention are typically from about 40 nucleotides in length to several thousand nucleotides in length. Usually, the nucleic acids are from about 80 to about 200 nucleotides.

After nucleic acid, e.g., DNA or RNA, has been isolated from blood plasma or serum, any of the conventional DNA or RNA detection methods can be used for the detection and quantification, e.g., amount or concentration, of nucleic acid. In a preferred embodiment, any means for detecting low copy number nucleic acids are used to detect the nucleic acids of the present invention. Means for detecting and quantifying low copy number nucleic acids include analytic biochemical methods such as electrophoresis, capillary electrophoresis, high performance liquid chromatography (HPLC), thin layer chromatography (TLC), hyperdiffusion chromatography, mass spectroscopy and the like. These methods are well known in the art and are thus not described in detail (See for example, U.S. Pat. Nos. 6,013,422, 6,261, 781, 6,268,146, or 5,885,775).

The methods of the present invention typically but not always rely on amplification or signal amplification methods for the detection of the nucleic acids. One of skill will recognize that amplification of target sequences in a sample may be accomplished by any known method, such as ligase chain reaction (LCR), Qβ-replicase amplification, transcription amplification, and self-sustained sequence replication, each of which provides sufficient amplification.

In one embodiment of the present invention, PCR is used to detect nucleic acids known to be present or suspected of being present in the blood plasma or serum of a stroke or cardiac ischemia patient. Typically, the nucleic acid will be present in the blood plasma or serum of a stroke or cardiac ischemia patient in greater concentrations than in the blood plasma or serum of a healthy individual. One of skill will know how to use standard methods to prepare primers for amplification of a known nucleic acid sequence and to subsequently amplify the sequence and visualize the products on a gel. The PCR process is well known in the art. For a review of PCR methods and protocols, see, e.g., Innis, et al. eds. *PCR Protocols. A Guide to Methods and Application* (Academic Press, Inc., San Diego, Calif. 1990). PCR reagents and protocols are also available from commercial vendors, such as Roche Molecular Systems.

The nucleic acids detected can be DNA or RNA molecules. In particular embodiments of the invention, RNA molecules are detected. The detected RNA molecules can also be RNA transcribed from genomic sequences, but which do not encode functional polypeptides. The first step in the amplification is the synthesis of a DNA copy (cDNA) of the region to be amplified. Reverse transcription can be carried out as a separate step, or in a homogeneous reverse transcription-polymerase chain reaction (RT-PCR), a modification of the polymerase chain reaction for amplifying RNA. Methods suitable for PCR amplification of ribonucleic acids are described in Romero and Rotbart in *Diagnostic Molecular Biology: Principles and Applications* pp. 401–406, Persing et al. eds., (Mayo Foundation, Rochester, Minn. 1993); Rotbart et al. U.S. Pat. No. 5,075,212 and Egger et al., *J. Clin. Microbiol.* 33:1442–1447 (1995)).

The primers used in the methods of the invention are preferably at least about 15 nucleotides to about 50 nucleotides in length, more preferably from about 15 nucleotides to about 30 nucleotides in length.

To amplify a target nucleic acid sequence in a sample by PCR, the sequence must be accessible to the components of the amplification system. In general, this accessibility is ensured by isolating the nucleic acids from the sample. A variety of techniques for extracting nucleic acids, from biological samples are known in the art and described above.

The first step of each cycle of the PCR involves the separation of the nucleic acid duplex formed by the primer extension. Once the strands are separated, the next step in PCR involves hybridizing the separated strands with primers that flank the target sequence. The primers are then extended to form complementary copies of the target strands. For successful PCR amplification, the primers are designed so that the position at which each primer hybridizes along a duplex sequence is such that an extension product synthesized from one primer, when separated from the template (complement), serves as a template for the extension of the other primer. The cycle of denaturation, hybridization, and extension is repeated as many times as necessary to obtain the desired amount of amplified nucleic acid (amplicon).

In the preferred embodiment of the PCR process, strand separation is achieved by heating the reaction to a sufficiently high temperature (~95° C.) for a sufficient time to cause the denaturation of the duplex but not to cause an irreversible denaturation of the polymerase (see U.S. Pat. No. 4,965,188). Template-dependent extension of primers in PCR is catalyzed by a polymerizing agent in the presence of adequate amounts of four deoxyribonucleoside triphosphates (typically dATP, dGTP, dCTP, and dTTP) in a reaction medium comprised of the appropriate salts, metal cations, and pH buffering system. Suitable polymerizing agents are enzymes known to catalyze template-dependent DNA synthesis. In the present invention, the initial template for primer extension is typically first strand CDNA that has been transcribed from RNA. Reverse transcriptases (RTs) suitable for synthesizing a cDNA from the RNA template are well known.

PCR is most usually carried out as an automated process with a thermostable enzyme. In this process, the temperature of the reaction mixture is cycled through a denaturing region, a primer annealing region, and an extension reaction region automatically.

The nucleic acids of the invention can also be detected using other standard techniques, well known to those of skill in the art. Although the detection step is typically preceded by an amplification step, amplification is not required in the methods of the invention. For instance, the nucleic acids can be identified by size fractionation (e.g., gel electrophoresis). The presence of different or additional bands in the sample as compared to the control is an indication of the presence of target nucleic acids of the invention. Alternatively, the target nucleic acids can be identified by sequencing according to well known techniques. Alternatively, oligonucleotide probes specific to the target nucleic acids can be used to detect the presence of specific fragments.

As explained in detail below, the size of the amplified fragments produced by the methods of the invention is typically sufficient to identify the presence of one or more bands associated with a particular disease. Thus, in some embodiments of the invention, size fractionation (e.g., gel electrophoresis) of the amplified fragments produced in a given sample can be used to distinguish the fragments associated with a particular disease. This is typically carried out by amplifying a control with the same primers used to amplify the sample of interest. After running the amplified sequences out in an agarose or polyacrylamide gel and staining, the nucleic acid, e.g., with ethidium bromide or other stains such as fluorescence dyes, e.g., SYBR green™ (Molecular Probes) according to well known techniques (see, Sambrook et al.), the pattern of bands in the sample and control are compared. The presence of different or additional bands in the sample as compared to the control, is an indication of the presence of a band associated with a disease.

Sequence-specific probe hybridization is a well known method of detecting desired nucleic acids in a sample comprising cells, biological fluids and the like. Under sufficiently stringent hybridization conditions, the probes hybridize specifically only to substantially complementary sequences. The stringency of the hybridization conditions can be relaxed to tolerate varying amounts of sequence mismatch. If the target is first amplified, detection of the amplified product utilizes this sequence-specific hybridization to insure detection of only the correct amplified target, thereby decreasing the chance of a false positive.

A number of hybridization formats are well known in the art, including but not limited to, solution phase, solid phase, oligonucleotide array formats, mixed phase, or in situ hybridization assays. In solution (or liquid) phase hybridizations, both the target nucleic acid and the probe or primers are free to interact in the reaction mixture. Techniques such as real-time PCR systems have also been developed that permit analysis, e.g., quantification, of amplified products during a PCR reaction. In this type of reaction, hybridization with a specific oligonucleotide probe occurs during the amplification program to identify the presence of a target nucleic acid. Hybridization of oligonucleotide probes ensure the highest specificity due to thermodynamically controlled two state transition. Examples for this assay formats are fluorescence resonance energy transfer hybridization probes, molecular beacons, molecular scorpions, and exonuclease hybridization probes (reviewed in Bustin S M. *J. Mol. Endocrin.* 25:169–93 (2000)).

In solid phase hybridization assays, either the target or probes are linked to a solid support where they are available for hybridization with complementary nucleic acids in solution. Exemplary solid phase formats include Southern or Northern hybridizations, dot blots, arrays, chips, and the like. In situ techniques are particularly useful for detecting target nucleic acids in chromosomal material (e.g., in metaphase or interphase cells). The following articles provide an overview of the various hybridization assay formats: Singer et al., *Biotechniques* 4:230 (1986); Haase et al., METHODS IN VIROLOGY, Vol. VII, pp. 189–226 (1984); Wilkinson, IN SITU HYBRIDIZATION, D. G. Wilkinson ed., IRL Press, Oxford University Press, Oxford; and NUCLEIC ACID HYBRIDIZATION: A PRACTICAL APPROACH, Hames, B. D. and Higgins, S. J., eds., IRL Press (1987).

The hybridization complexes are detected according to well known techniques and are not a critical aspect of the present invention. Nucleic acid probes capable of specifically hybridizing to a target can be labeled by any one of several methods typically used to detect the presence of hybridized nucleic acids. One common method of detection is the use of autoradiography using probes labeled with $^3$H, $^{125}$I, $^{35}$S, $^{14}$C, or $^{32}$P, or the like. The choice of radioactive isotope depends on research preferences due to ease of synthesis, stability, and half-lives of the selected isotopes. Other labels include compounds (e.g., biotin and digoxigenin), which bind to antiligands or antibodies labeled with fluorophores, chemiluminescent agents, and enzymes. Alternatively, probes can be conjugated directly with labels such as fluorophores, chemiluminescent agents or enzymes. The choice of label depends on sensitivity required, ease of conjugation with the probe, stability requirements, and available instrumentation.

The probes and primers of the invention can be synthesized and labeled using well-known techniques. Oligonucleotides for use as probes and primers may be chemically synthesized according to the solid phase phosphoramidite triester method first described by Beaucage, S. L. and Caruthers, M. H., 1981, *Tetrahedron Letts.*, 22(20):1859–1862 using an automated synthesizer, as described in Needham-VanDevanter, D. R., et al. 1984, *Nucleic Acids Res.*, 12:6159–6168. Purification of oligonucleotides can be performed, e.g., by either native acrylamide gel electrophoresis or by anion-exchange HPLC as described in Pearson, J. D. and Regnier, F. E., 1983, *J. Chrom.*, 255:137–149.

Detection of the nucleic acid sequences can also be accomplished by means of signal amplification techniques. For example, the branched DNA assay uses a specific probe to a target sequence to identify the presence of the target. The signal is amplified by means of modifications made to the probe which allow many fluorescent detector DNA molecules to hybridize to a target nucleic acid (Chiron Diagnostics).

Any nucleic acid species present in the blood plasma or serum sample of a stroke or cardiac ischemia patient can be detected by the methods of the present invention and used as a marker to evaluate stroke or cardiac ischemia in the patient. Typically, the nucleic acid species will be present in the blood plasma or serum of a stroke or cardiac ischemia patient in greater concentrations than in the blood plasma or serum of a healthy individual. Examples of nucleic acids species include, but are not limited to, the human leukocyte antigen (HLA) locus, Y chromosomal genes (Lee T H et al., *Transfusion* 2001 ; 41 :276–282), blood group antigen genes like RHD (Lo Y M D et al., *N. Engl. J. Med.* 1998; 339:1734–1738), and mitochondrial DNA (Zhong S et al., *J. Clin. Pathol.* 2000; 53:466–469) and mRNA (Poon L L M et al., *Clin. Chem.* 2000; 46:1832–1834; Chen X Q et al., *Clin. Cancer Res.* 6:3823–3826). Another exemplary marker used in the methods of the present invention is the beta-globin DNA. Probes and primers for the detection of beta-globin DNA can be synthesized using well-known techniques and are well known in the art, (see Example 3). Probes and primers for the detection of other known nucleic species suspected or known to be present in the blood plasma or serum sample of a stroke or cardiac ischemia patient can be synthesized using well known techniques.

Methods of Evaluating Stroke or Cardiac Ischemia

Once the nucleic acid present in the sample from a patient has been detected and quantified, the quantity, e.g., concentration or amount, of nucleic acid in the sample is compared to a control. The skilled practitioner can use the comparison to evaluate a disease condition in a patient. For example, a different concentration of nucleic acid in the sample from a patient than in the control indicates an abnormality in the patient. The greater the amount of nucleic acid in the sample than in the control, the greater the abnormality. By comparing the relative differences between the sample and control, a skilled practitioner can determine if an individual is at risk for developing a disease, e.g., stroke or cardiac ischemia. By comparing the relative differences between the sample and control, a skilled practitioner can diagnose the disease, determine the stage of disease, or determine prognosis of the disease in the patient.

For example, in some patients, the amount or concentration of nucleic acid in the sample will be the same as in the control. In some patients, the amount or concentration of nucleic acid in the sample will be slightly higher than in the control, e.g., 25% higher. In other patients, the amount or concentration of nucleic acid in the sample will be 50% higher than in the control. In yet even other patients, the amount or concentration of nucleic acid in the sample will be double or quadruple the amount in the control. Depending upon the relative difference between the amount of nucleic acid in the sample from a patient and in the control, a patient may be subject to different lengths of hospital stay or different treatment or monitoring plans. For example, if the amount or concentration of nucleic acid in the sample is equal to that in the control, a patient may be given a good prognosis and discharged from a hospital. In another example, if the amount or concentration of nucleic acid in the sample is only slightly higher than in the control, a patient may be discharged from a hospital but subject to further monitoring. If the amount or concentration of nucleic acid in the sample is much higher than that in the control, e.g., 2 to 10 fold higher, a patient may be given a poor prognosis and subject to more aggressive treatment.

Using the methods of the present invention, a skilled practitioner will know how to identify and quantify specific nucleic acids present in a stroke or cardiac ischemia patient and evaluate the disease condition in the patient. For example, in one embodiment of the present invention, it was determined that plasma or serum beta-globin DNA concentrations of greater than 1400 kilogenome-equivalents per liter in a patient are indicative of an increased possibility of death in stroke patients. It was further determined that for every 600 kilogenome-equivalents per liter increase in plasma beta-globin DNA, the risk is approximately doubled.

Informatics

In general, bioinformatics is the study and application of computer and statistical techniques to the management of biological information. The development of systems and methods to create and search databases containing biological information including concentrations of circulating nucleic acids in the blood plasma or serum of healthy and diseased individuals and the ability to use that biological information to evaluate disease conditions is increasingly important.

Thus, in one embodiment, the present invention provides a method for populating a database for further medical characterization. The method includes populating a database with the blood plasma or serum nucleic acid concentrations of patients suspected of having, known to have, or at risk of having specific diseases and using a software program to compare those concentrations to controls. The present invention also provides a method for creating the control by amassing data from healthy and diseased individuals and corresponding levels of nucleic acid concentration in their blood plasma or serum to absence or presence of disease, severity of disease, prognosis of disease, appropriate treatment plans for disease, or risk stratification.

In another embodiment, the present invention also provides an apparatus for automating the methods of the present invention, the apparatus comprising a computer and a software system capable of comparing inputed blood plasma or serum nucleic acid concentrations of patients suspected of having, known to have, or at risk of having specific diseases with controls. The nucleic acid concentration data is inputted in computer-readable form and stored in computer-retrievable form. The present invention also provides computer-readable medium encoded with a data set comprising concentration of blood plasma or serum nucleic acid levels in patients suspected of having, known to have, or at risk of having specific diseases.

The methods described herein for quantifying nucleic acid concentrations in the blood plasma or serum of individuals provide information which can be correlated with pathological conditions, predisposition to disease, therapeutic monitoring, prognosis, risk stratification, among others. Although the data generated from the methods of the invention is suited for manual review and analysis, in a preferred embodiment, prior data processing using high-speed computers is utilized.

An array of methods for indexing and retrieving biomolecular information is known in the art. For example, U.S. Pat. Nos. 6,023,659 and 5,996,712 disclose a relational database system for storing biomolecular sequence information in a matter that allows sequences to be catalogued and searched according to one or more protein function hierarchies.

The invention also provides for the storage and retrieval of a collection of blood plasma or serum nucleic acid concentrations in a computer data storage apparatus, which can include magnetic disks, optical disks, magneto-optical disks, DRAM, SRAM, SGRAM, SDRAM, RDRAM, DDR RAM, magnetic bubble memory devices, and other data storage devices, including CPU registers and on-CPU data storage arrays.

The invention also preferably provides a magnetic disk, such as an IBM-compatible (DOS, Windows, Windows95/98/2000, Windows NT, OS/2) or other format (e.g., Linux, SunOS, Solaris, AIX, SCO Unix, VMS, MV, Macintosh, etc.) floppy diskette or hard (fixed, Winchester) disk drive, comprising a bit pattern encoding data collected from the methods of the present invention in a file format suitable for retrieval and processing in a computerized sequence analysis, comparison, or relative quantitation method.

The invention also provides a network, comprising a plurality of computing devices linked via a data link, such as an Ethernet cable (coax or 10BaseT), telephone line, ISDN line, wireless network, optical fiber, or other suitable signal tranmission medium, whereby at least one network device (e.g., computer, disk array, etc.) comprises a pattern of magnetic domains (e.g., magnetic disk) and/or charge domains (e.g., an array of DRAM cells) composing a bit pattern encoding data acquired from the methods of the invention.

The invention also provides a method for transmitting concentration data that includes generating an electronic signal on an electronic communications device, such as a modem, ISDN terminal adapter, DSL, cable modem, ATM switch, or the like, wherein the signal includes (in native or encrypted format) a bit pattern encoding data collected from the methods of the present invention.

In a preferred embodiment, the invention provides a computer system for comparing nucleic acid concentration in blood plasma or serum of disease individuals to a control. A central processor is preferably initialized to load and execute the computer program for alignment and/or comparison of the assay results. Data is entered into the central processor via an I/O device. Execution of the computer program results in the central processor retrieving the data from the data file.

The target data or record and the computer program can be transferred to secondary memory, which is typically random access memory (e.g., DRAM, SRAM, SGRAM, or SDRAM). For example, a central processor can be a conventional computer (e.g., Intel Pentium, PowerPC, Alpha, PA-8000, SPARC, MIPS 4400, MIPS 10000, VAX, etc.); a program can be a commercial or public domain molecular biology software package (e.g., UWGCG Sequence Analysis Software, Darwin); a data file can be an optical or magnetic disk, a data server, a memory device (e.g., DRAM, SRAM, SGRAM, SDRAM, EPROM, bubble memory, flash memory, etc.); an I/O device can be a terminal comprising a video display and a keyboard, a modem, an ISDN terminal adapter, an Ethernet port, a punched card reader, a magnetic strip reader, or other suitable I/O device.

The invention also preferably provides the use of a computer system, such as that described above, which comprises: (1) a computer; (2) a stored bit pattern encoding a collection of nucleic acid concentrations obtained by the methods of the invention, which may be stored in the computer; (3) a comparison control (4) a program for comparison.

It is understood that the examples and embodiments described herein are for illustrative purposes only and that various modifications or changes in light thereof will be suggested to persons skilled in the art and are to included within the spirit and purview of this application and are considered within the scope of the appended claims. All publications, patents, and patent applications cited herein are hereby incorporated by reference in their entirety for all purposes.

EXAMPLES

Example 1

Detection of the Beta Globin Gene

The present invention provides a simple method for testing blood plasma or serum for circulating nucleic acids. Using the methods of the present invention, the beta globin gene was detected in the blood plasma and serum samples obtained from stroke patients. A blood sample was drawn from a patient, DNA was extracted, and measured using PCR. Primers specific for the beta-globin gene were used.

Example 2

Study Design and Patients

Approval was obtained from the Institutional Review Board of the Chinese University of Hong Kong to conduct a prospective study investigating the role of plasma DNA in the diagnosis and prognosis of patients presenting with stroke-like syndromes at the Prince of Wales Hospital. The Prince of Wales Hospital is a 1400-bed university hospital based in the New Territories of Hong Kong which serves a population of approximately 1 500 000.

Eligible patients aged $\geq 18$ years presenting to the emergency department with a stroke-like syndrome were recruited consecutively into the study. Exclusion criteria included multiple trauma, craniocerebral or cervical trauma, meningitis, encephalitis or other sepsis, hypertensive encephalopathy, intracranial tumor, seizures with persistent neurological signs (Todd's paralysis), Bell's palsy, migraine, metabolic disturbances (for example hypoglycemia, hyperglycemia), post-cardiac arrest, drug overdose, endocrine disorders (for example myxedema), renal failure, psychiatric syndromes, or shock with hypoperfusion. Patients were also excluded if the time from symptom onset to blood sampling was greater than 24 hours. Informed, written consent was obtained either from the patient or a relative in all cases. Healthy age and sex-matched patients were recruited as controls.

Stroke was defined as the acute occurrence of focal neurological signs lasting for more than 24 hours in a different neuroanatomical location from that of any previous stroke, or worsening of an existing deficit that lasted for more than one week, or more than 24 hours if accompanied by a new lesion on neuroimaging. Stroke-like syndrome was defined according to the following criteria: firstly, if the patient had a facial droop, arm drift or weakness, or abnormal speech (compatible with the Cincinnati Prehospital Stroke Scale); secondly, if the patient had an altered level of consciousness with no obvious associated seizures, hyperglycemia or hypoglycemia (compatible with the Los Angeles Prehospital Stroke Scale).

Demographic and previous medical data were collected including age, sex, symptom onset time, history of previous stroke, seizures, hypertension, diabetes mellitus, ischemic heart disease, atrial fibrillation, hyperlipidemia, smoking, antithrombotic and other medication. An assessment of each patient's previous health was made using the Pre-Stroke Modified Rankin Scale, a simplified overall assessment of function in which a score of 0 indicates the absence of symptoms and a score of 5 indicates severe disability. In order to determine the exact nature and cause of the stroke-like syndrome, patients received a standard clinical, laboratory and imaging workup, including cerebral computed axial tomography (CT) without contrast enhancement and magnetic resonance imaging (MRI) including a diffusion-weighted MRI study. All CT scans was performed with a GE HiSpeed Advantage Unit. Axial 5/5 mm scans were done for the posterior cranial fossa and 10/10 mm scans were then performed up to the vortex space. MRI scans were performed with a 1.5 T scanner (Sonata, Siemens). The sequences included SE T1 axial (TR/TE/NEX 425/14/2 slice thickness 5 mm, slice gap 0.5 mm 192×256 matrix), TSE T2 axial (TR/TE/NEX 2500/120/1 slice thickness 5 mm slice gap 0.5 mm 192×256 matrix), and single shot EPI diffusion weighted axial images (TR=180 msec, TE=122 msec, slice thickness 5 mm, matrix 128×128, EPI factor of 90). Three different diffusion gradients were used, giving b values of 0, 500 s/mm$^2$ and 1000 s/mm$^2$. The volume of infarct was measured on both CT films and MRI diffusion scans, whilst the volume of an acute hematoma was measured on CT films and T1 weighted MRI scans. CT (N=88) and MRI scans (N=71) were not possible for all cases as some patients were too ill for two scans and some patients had contraindications for MRI.

Patients were classified as having a transient ischemic attack (TIA) if their symptoms and signs resolved within 24 hours. Stroke cases were classified to one of two groups: intracerebral hemorrhage or cerebral infarction. Non-hemorrhagic cases were further classified according to definitions used in the TOAST trial.

The severity of stroke was assessed clinically using two methods. The National Institutes of Health Stroke Scale (NIHSS) is a 42-point scale that quantifies neurologic deficit in 11 categories such that normal function with no deficit receives a score of zero. The Glasgow Coma Score is a 13-point score which ranges from 3 to 15 and assesses visual, motor and verbal responses to stimulus such that a score of 15 gives a normal response and 3 is associated with severe dysfunction.

Example 3

Preparation of Plasma DNA and Real-Time PCR

A 10 mL blood sample was withdrawn from the antecubital vein of each patient, collected into tubes containing ethylene-diamine-tetra-acetic acid, centrifuged at 1500×g for 5 minutes, and plasma was then transferred into plain polypropylene tubes, and stored at −80° C. pending further processing.

DNA was extracted from 200 µl plasma samples using a QIAamp Blood Kit (Qiagen, Hilden, Germany) according to the "blood and body fluid protocol" as recommended by the manufacturer. Theoretical and practical aspects of real-time quantitative PCR have been described in detail elsewhere and the whole process takes about three hours (Lo Y M D, et al. *Am. J. Hum. Genet.* 1998; 62:768–75. Heid C A, Stevens J, Livak K J, Williams P M. Real time quantitative PCR. *Genome Res.* 1996; 6:986–94; Luthra R. et al., *Am. J. Pathol.* 1998; 153:63–8; Holland et al., *Proc. Natl. Acad. Sci. U.S.A.* 1991; 88:7276–80)

Plasma DNA was measured using a real-time quantitative PCR assay for the beta-globin gene which is present in all nucleated cells of the body [11]. The beta-globin PCR system consists of the amplification primers: SEQ ID NO:1-beta-globin-354F; 5'-GTG CAC CTG ACT CCT GAG GAG A-3'; SEQ ID NO: 2-beta-globin-455R; 5'-CCT TGA TAC CAA CCT GCC CAG-3'; SEQ ID NO: 3-Dual labeled fluorescent PCR probe beta globin-402T; 5'-(VIC)AAG GTG AAC GTG GAT GAA GTT GGT GG(TAMRA)-3' [11]. The PCR probe contained a 3'-blocking phosphate group to prevent probe extension during PCR.

When applied to serial dilutions of human genomic DNA, this real-time beta globin quantitative PCR assay was able to detect the DNA equivalent from a single cell. The expression of quantitative results as kilogenome-equivalents per liter was as previously described (Lo Y M D, et al. *Am. J. Hum. Genet.* 1998; 62:768–75). One genome-equivalent was defined as the amount of a particular target sequence contained in a single diploid human cell.

Example 4

Outcome and Evaluation

The primary outcome measures were mortality and Post-Stroke Modified Rankin Score at six months after the onset of symptoms. Other outcome measures included mortality in hospital or within 28 days whichever was sooner, and loss of quality of life defined as a six-month Post-Stroke Modified Rankin Score minus their Pre-Stroke Modified Rankin Score.

Statistical Analysis

Descriptive statistics and data comparison tests—chi-squared, Fisher's exact, Mann-Whitney and Kruskal-Wallis tests—were carried out using Statview® for Windows version 5.0 Statistical Analysis Software (Abacus Concepts, SAS Institute, Cary N.C., USA) as appropriate. Correlations were determined using Spearman Rank or Kruskall-Wallis tests whilst Receiver Operating Characteristic (ROC) curve analysis was carried out using the MedCalc 5.0 software. Multiple logistic regression analysis using backward stepwise selection procedures to exclude those variables with P values >0.5 was built, and P values are calculated using the Wald test. Hosmer and Lemeshow test was used to confirm the goodness of fit.

Characteristics of 88 adult patients who were enrolled in the study with a stroke-like syndrome are shown in Table 1. Although the majority of patients were elderly and had a number of risk factors for stroke, 71 (81%) had no significant health disability prior to their acute admission as assessed using the Pre-Stroke Modified Rankin Score. Six patients died within 28 days of hospital admission and 11 within six months. The healthy control group did not differ significantly from the patient group in either age or sex.

TABLE 1

CHARACTERISTICS OF THE 88 PATIENTS PRESENTING TO HOSPITAL WITH STROKE*

| CHARACTERISTICS | VALUE |
|---|---|
| Age (yr) | 74 [16] 50–92 |
| Male sex - no. of patients (%) | 45 (51) |
| Stroke risk factors - no. of patients (%) | |
| Hypertension | 53 (60) |
| Diabetes mellitus | 21 (24) |
| Ischemic Heart Disease | 11 (13) |
| Atrial Fibrillation | 15 (17) |
| Hyperlipidemia | 9 (10) |
| Active smoking | 18 (21) |
| Ex-smoking | 22 (25) |
| Previous stroke | 24 (27) |
| Pre-Stroke Modified Rankin Score - no. of patients (%) | |
| Asymptomatic | 71 (81) |
| No significant disability | 14 (16) |
| Slight disability | 2 (2) |
| Moderate disability | 0 |
| Moderately severe disability | 1 (1) |
| Severe disability | 0 |
| Time from onset of symptoms to blood sample (hrs) | 8 [12] 1–24 |
| Pulse rate (per minute) | 77 [22] 24–172 |
| Blood pressure (mm Hg) | |
| Systolic | 169 [55] 100–272 |
| Diastolic | 88 [26] 40–142 |
| Blood glucose (mmol/L) † | 6.8 [3.5] 4.2–20 |
| Glasgow Coma Score - no. of patients (%) | |
| 3–8 | 4 (5) |
| 9–12 | 9 (10) |
| 13–15 | 75 (85) |
| NIHSS score - no. of patients (%)‡ | |
| 0–1 | 7 (8) |
| 2–8 | 40 (46) |
| 9–40 | 41 (47) |
| Stroke Types - no. of patients (%) | |
| Infarct | 70 (80) |
| Hemorrhage | 11 (13) |
| Transient Ischemic Attack - no. of patients (%) | 7 (8) |
| TOAST - no. of patients (%) § | |
| Cardioembolism | 8 (9) |
| Hemorrhage | 11 (13) |
| Large artery atherosclerosis | 29 (33) |
| Small vessel occlusion or lacunae | 3 (3) |
| Undetermined | 37 (42) |

*All continuous data are expressed as medians [interquartile range] range. Numbers may not sum to 100 because of rounding, multiple factors (for example risk factors) or absent data.
† To convert values for glucose to milligrams per deciliter, multiply by 18.014772.
‡NIHSS, National Health Institute Stroke Scale.
§ TOAST, Trial of Org 10172 in Acute Stroke Treatment [29]

Univariate Analysis of Plasma DNA and Other Variables with Outcome

Median plasma DNA levels were two-fold higher in patients who died compared with those who survived at discharge (2126 kilogenome-equivalents per liter versus 1008 kilogenome-equivalents per liter; P=0.0016, FIG. 1) and were also higher in patients who died compared with those who survived at six months (1979 kilogenome-equivalents per liter versus 1004 kilogenome-equivalents per liter, P=0.0003, Table 2). There was no difference in median plasma DNA levels between the control group and those patients who were discharged (1030 kilogenome-equivalents per liter versus 1012 kilogenome-equivalents per liter; P=0.3762) but there was a significant difference in median plasma DNA levels between healthy control patients and those patients who died within 28 days (1030 kilogenome-equivalents per liter versus 2273 kilogenome-equivalents per liter; P=0.0476). Median plasma DNA levels taken within the first three hours of symptoms were fivefold higher in patients who died than in those who survived (6205 kilogenome-equivalents per liter versus 1334 kilogenome-equivalents per liter; P=0.0335), whilst the highest single result of 8272 kilogenome-equivalents per liter occurred in a patient who later died. In the univariate analysis, no other independent variable discriminated those patients who died from those who survived.

Figure 2:
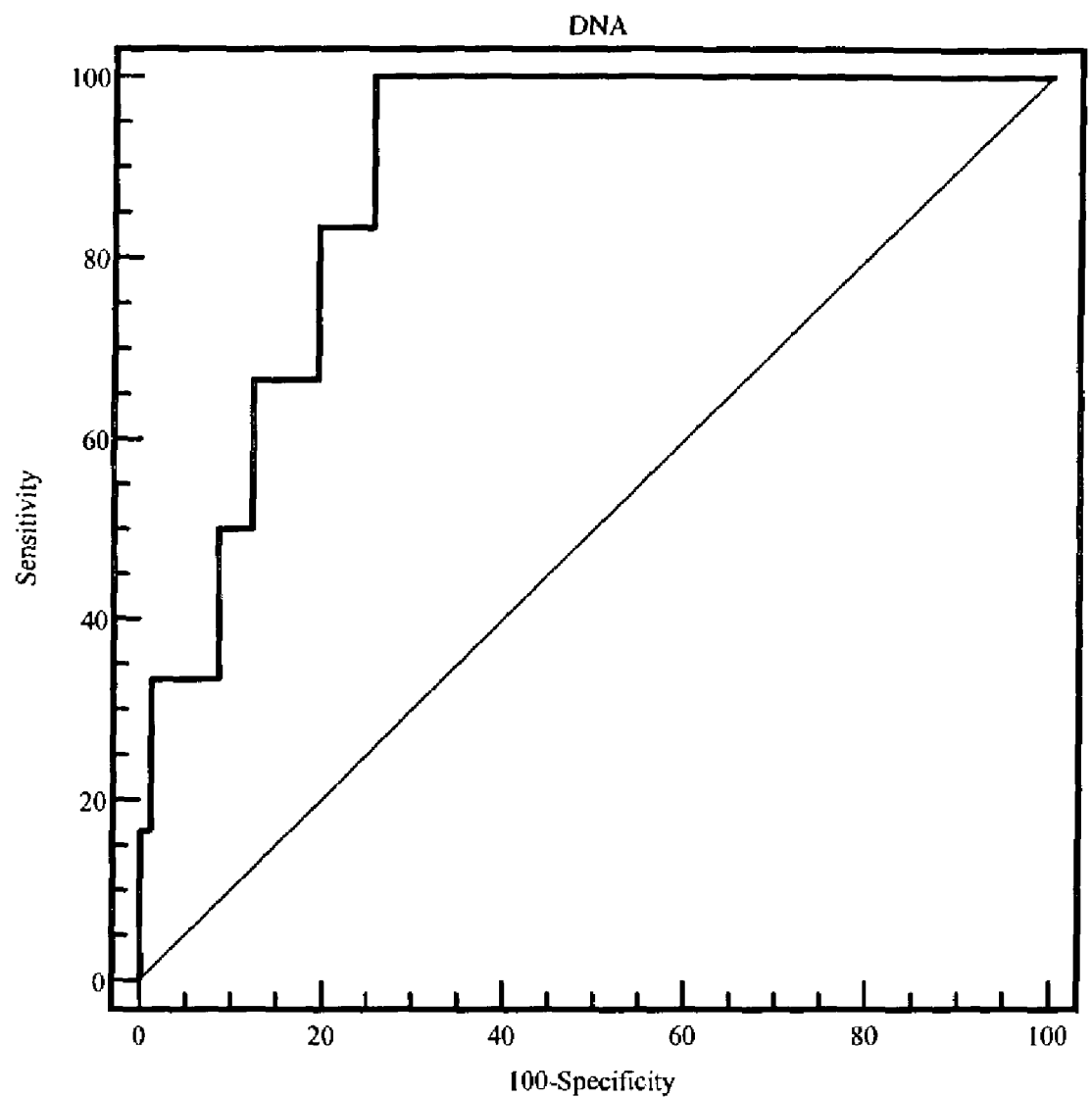
FIG. 2. Receiver Operator Characteristic curve analysis of plasma DNA concentrations for the prediction of mortality within 28 days of onset of symptoms. Values indicated on the x- and y-axes are expressed in percentages. Seven patients died. The area under the curve is 0.888 (95% CI 0.803 to 0.945).

The ROC curve analysis for comparing the sensitivity and specificity of plasma DNA levels in the six patients who died within 28 days of hospital admission are shown in FIG. 2. The area under the curve was 0.888 (95% CI 0.803 to 0.945). At a plasma DNA cut off of 1400 kilogenome-equivalents per liter, the optimal sensitivity and specificity were 100% (95% CI 100.0 to 100.0) and 74.4% (95% CI 63.6 to 83.4), respectively. At this cut off, the odds ratio was 3.90 and the negative predictive value was 100%. Median plasma DNA levels were 30% higher in patients with six month modified Post-Rankin Score >2 compared with patients who scored ≦2 (Table 2). In the univariate analysis, NIHSS and MRI lesion volume also discriminated these two groups of patients. Plasma DNA levels correlated with the Glasgow Coma Score (H=12.127; P=0.0023, Kruskal-Wallis test), cerebral hemorrhage volume (r=0.664; P=0.0276, Spearman Rank), Post-Stroke Modified Rankin Score (H=21.808; P=0.0013, Kruskal-Wallis) and quality of life loss (H=20.696; p=0.0042, Kruskal-Wallis).

Logistic Regression Model for Predicting Six-Month Mortality and Modified Post-Rankin Score >2

Table 3 shows the adjusted odds ratios of independent variables for predicting six-month mortality and a Post-Stroke Modified Rankin Score of >2. Lesion volume as measured by CT and plasma DNA levels were the only significant variables for predicting six-month mortality. NIHSS groups >8 and plasma DNA levels were the only significant variables for predicting a six-month modified Post-Stroke Modified Rankin Score of >2. For every 460 kilogenome-equivalents per liter increase in plasma DNA, the associated increased risk of death within six months of stroke is 58.5% (95% CI 5% to 239%) whilst for every 1.3 $cm^3$ increase in lesion volume as determined by CT, the increased risk of death within six months of stroke is 14% (95% CI 3.2% to 125%). For every 600 kilogenome-equivalents per liter increase in plasma DNA, the associated increased risk of a six-month Post-Stroke Modified Rankin Score of >2 is 82% (95% CI 0% to 331%).

TABLE 2

COMPARISON OF FACTORS FOR PREDICTING SIX-MONTH MORTALITY AND POST-STOKE MODIFIED RANKIN SCORE IN 88 PATIENTS WITH STROKE*

| FACTOR | MORTALITY | | | POST-STROKE MODIFIED SCORE | | |
|---|---|---|---|---|---|---|
| | SURVIVED (N = 77) | DIED (N = 11) | P VALUE † | ≦2 (N = 48) | >2 (N = 40) | P VALUE † |
| Age - years | 73 (16) 50–92 | 75 (11.5) 55–90 | 0.1633 | 72 (17) 50–91 | 76 (14) 54–92 | 0.1262 |
| Male Sex - no. of patients (%) | 38 (49) | 7 (64) | 0.3750 | 24 (50) | 24 (60) | 0.8153 |
| Time from symptom onset to blood sampling - hours | 8.0 (12.0) 0.5–24 | 6.5 (13.0) 0.5–21 | 0.6050 | 10.0 (13.0) 1.5–22.0 | 7.0 (9.0) 0–24 | 0.2149 |
| Pre-Stroke Modified Rankin Scale - no. of patients (%) | | | | | | |
| 0–1 | 74 (96) | 11 (100) | 1.0000 | 47 (98) | 38 (95) | 0.5888 |
| 2–4 | 3 (4) | — | | 1 (2) | 2 (5) | |
| National Institute for Health Stroke Scale Score - no. of patients (%) | | | | | | |
| 0–1 | 7 (9) | — | 0.3660 | 5 (10) | 2 (5) | 0.0068 |
| 2–8 | 36 (47) | 4 (36) | | 28 (58) | 12 (30) | |
| >8 | 34 (44) | 7 (64) | | 15 (31) | 26 (65) | |
| Systolic blood pressure - mmHg | 170 (57) 100–263 | 160 (49) 114–272 | 0.8648 | 171 (52) 102–263 | 160 (59) 100–272 | 0.7217 |
| Diastolic blood pressure - mmHg | 87 (28) 40–142 | 94 (23) 70–134 | 0.1192 | 88 (23) 40–136 | 91 (32) 53–142 | 0.4893 |
| Risk Factors - no. of patients (%) | | | | | | |
| Hypertension | 46 (60) | 7 (64) | 1.0000 | 28 (58) | 25 (63) | 0.6909 |
| Diabetes Mellitus | 20 (26) | 1 (9) | 0.4480 | 11 (23) | 10 (25) | 0.8194 |
| Ischemic Heart Disease | 8 (10) | 3 (27) | 1.0000 | 5 (10) | 6 (15) | 0.5174 |
| Atrial Fibrillation | 11 (14) | 4 (36) | 1.0000 | 6 (13) | 9 (23) | 0.2142 |
| Prior Stroke | 19 (25) | 4 (36) | 1.0000 | 13 (27) | 10 (25) | 0.8247 |
| Lesion volume on MRI - $cm^3$ ‡ | 1.7 (15.1) 0–220.7 | 5.5 (55.4) 0.8–105.1 | 0.3557 | 1.1 (8.8) 0–193.3 | 5.6 (43.6) 0–220.7 | 0.0514 |
| Lesion volume on CT - $cm^3$ § | 0.1 (3.7) 0–225.0 | 70.0 (234.8) 0–518.5 | 0.1253 | 0.1 (3.1) 0–151.2 | 0.6 (50.0) 0–518.5 | 0.1617 |
| Plasma DNA - $x10^3$ kilogenome-equivalents per litre ¶ | 1.0 (0.6) 0.3–7.1 | 2.0 (1.9) 0.9–8.3 | 0.0003 | 1.0 (0.5) 0.3–5.2 | 1.3 (1.3) 0.3–8.3 | 0.0237 |

*Continuous variables are presented as medians (interquartile range) and minimum to maximum range. Categorical variables are presented as values (percentages).
† P values are derived using the Mann-Whitney test, $\chi^2$ test or Fisher's exact test as appropriate.
‡ MRI, magnetic resonance imaging.
§ CT, computerized tomography.
¶ DNA, deoxyribonucleic acid.

TABLE 3

LOGISTIC REGRESSION MODEL OF FACTORS
FOR PREDICTING SIX-MONTH MORTALITY AND POST-STROKE
MODIFIED RANKIN SCORE > 2 AFTER STROKE (N = 88)*

| FACTOR | ADJUSTED ODDS RATIO FOR MORTALITY (95% CI) | P VALUE | ADJUSTED ODDS RATIO FOR POST-STROKE MODIFIED RANKIN SCORE > 2 (95% CI) | P VALUE |
| --- | --- | --- | --- | --- |
| Lesion volume on CT- ×10 cm$^3$ † | 1.135 (1.032–1.250) | <0.01 | — | — |
| Plasma DNA- ×10$^3$ kilogenome-equivalents per liter ‡ | 1.585 (1.052–2.389) | 0.03 | 1.819 (1.000–3.312) | 0.05 |
| NIHSS group > 8 § | — | — | 3.419 (1.360–8.594) | <0.01 |

*Logistic regression model using backward stepwise selection procedures was built using variables from Table 2. Only lesion volume as determined using computerized tomography scanning and plasma DNA levels were significantly associated with six-month mortality, whilst only NIHSS group > 8 and plasma DNA levels were significantly associatedwith a Post-Stroke Modified Rankin Score of >2. The Hosmer and Lemeshow goodness-of-fit test was used to confirm that the models fitted the data (Mortality: $\chi^2$ test = 5.432; P = 0.711; Post-Stroke Modified Rankin Score: $\chi^2$ test = 5.402; P = 0.714).
† CT, computerized tomography.
‡ DNA, deoxyribonucleic acid.
§ NIHSS, National Health Institute Stroke Scale

What is claimed is:

1. A method of evaluating the disease condition of stroke in a stroke patient, the method comprising:
   (i) obtaining a sample of blood plasma or serum from a stroke patient,
   (ii) detecting the quantity of DNA in the sample, and
   (iii) evaluating the disease condition of stroke by comparing the quantity of DNA in the sample to a control, wherein the disease condition is post-stroke mortality or post-stroke morbidity as indicated by a six-month Post-Stroke Modified Rankin Score, whereby an increase in the quantity of DNA indicates an increase in post-stroke mortality or post-stroke morbidity.

2. The method of claim 1, wherein the disease condition is post-stroke mortality.

3. The method of claim 2, wherein the post-stroke mortality is 28-day post-stroke mortality.

4. The method of claim 2, wherein the post-stroke mortality is six-month post-stroke mortality.

5. The method of claim 1, wherein the disease condition is post-stroke morbidity as indicated by a six-month Post-Stroke Modified Rankin Score.

6. The method of claim 1, wherein the DNA detected is selected from the group consisting of DNA sequences from the beta-globin, RHD, and albumin genes.

7. The method of claim 6, wherein the DNA detected is DNA sequences of the beta globin gene.

8. The method of claim 7, wherein the detection step further comprises contacting the sample with a polynucleotide that selectively hybridizes to the beta-globin gene.

9. The method of claim 1, further comprising the step of amplifying the DNA.

10. The method of claim 9, wherein the DNA is amplified using PCR.

11. The method of claim 10, wherein the DNA is amplified using real-time PCR.

12. The method of claim 9, wherein the DNA is amplified using the primers disclosed in SEQ ID NO:1 and SEQ ID NO:2.

13. The method of claim 1, wherein the sample was obtained within 24 hours of onset of stroke-like symptoms in the patient.

14. The method of claim 1, wherein the sample was obtained within 3 hours of onset of stroke-like symptoms in the patient.

* * * * *